United States Patent [19]

Cardin et al.

[11] Patent Number: 5,670,144
[45] Date of Patent: Sep. 23, 1997

[54] ANTI-HERPES VIRUS AND CYTOMEGALOVIRUS POLYESTER OLIGOMERS

[75] Inventors: Alan D. Cardin; Richard L. Jackson, both of Cincinnati, Ohio; Michael J. Mullins, Midland, Mich.

[73] Assignees: Merrell Pharmaceuticals Inc., Cincinnati, Ohio; The Dow Chemical Company, Midland, Mich.

[21] Appl. No.: 469,390

[22] Filed: Jun. 6, 1995

Related U.S. Application Data

[60] Division of Ser. No. 965,248, Jul. 8, 1991, which is a continuation-in-part of Ser. No. 710,370, Jun. 10, 1991, Pat. No. 5,276,182, which is a continuation-in-part of Ser. No. 549,782, Jul. 9, 1990, abandoned.

[51] Int. Cl.$^6$ .................................................. A61K 31/74
[52] U.S. Cl. ................................... 424/78.08; 514/934
[58] Field of Search ................................ 514/517, 934; 424/78.08

[56] References Cited

U.S. PATENT DOCUMENTS

| | | | |
|---|---|---|---|
| 2,833,744 | 5/1958 | Neher | 260/775 |
| 3,528,949 | 9/1970 | Rutledge | 260/77.5 |
| 4,104,262 | 8/1978 | Schade | 528/294 |
| 4,471,110 | 9/1984 | Christell | 528/337 |
| 4,604,404 | 8/1986 | Munson et al. | 514/494 |
| 4,783,446 | 11/1988 | Neushul . | |
| 4,824,916 | 4/1989 | Kershner et al. | 510/420 |
| 4,895,660 | 1/1990 | Kershner et al. | 210/640 |
| 4,966,894 | 10/1990 | Herr et al. . | |
| 5,424,063 | 6/1995 | Cardin et al. . | |

FOREIGN PATENT DOCUMENTS

| | | |
|---|---|---|
| 0498095 | 2/1991 | European Pat. Off. . |
| 100457185 | 1/1992 | European Pat. Off. . |
| 2669535 | 5/1992 | France . |
| 900094 | 10/1990 | South Africa . |
| 781479 | 8/1957 | United Kingdom . |
| 907829 | 10/1962 | United Kingdom . |
| 8800828 | 2/1988 | WIPO . |
| 9200749 | 1/1992 | WIPO . |
| 9314146 | 7/1993 | WIPO . |
| 9316992 | 9/1993 | WIPO . |

OTHER PUBLICATIONS

R.M. Ottenbrite, ACS Symposium Series #186, pp. 205–220 (1982) "The Antitumor and Antiviral Effects of Polycarboxylic Acid Polymers".

G. Odian, Principles of Polymerization, 2d, pp. 20–25 (1981).

Ahmed, et al., Antiviral Chemistry & Chemotherapy, (1995) "Potent Inhibition of Herpes Simplex Virus by MDL101028 a Novel Biphenyl Disulphonic Acid Co–polymer".

Antiviral Research, 19 (1992) Sulfonic acid polymers as a new class of human immunodeficiency virus inhibitors, Prem Mohan, et al., pp. 139–150.

Cardin et al., "Stilbene Disulfonic Acids. CD4 Antagonists that Block Human Immunodeficiency Virus Type–1 Growth at Multiple Stages of the Viral Like Cycle" J. Biol. Chem (1991), 266(20), 1335563.

Hofferek et al., Chemical Abstracts vol. 114: 180333q (1990).

Akerfeldt, et al., Chemical Abstracts vol. 75: 72945H (1971).

Taylor et al, "Potent Inhibition of Human Immunodeficiency Virus (HIV) by MDL 101028, a Novel Supphonic Acid Polymer".

Antiviral Research, 18 (1992), Sulfonic acid polymers as a new class of human immunodefi–ciency virus inhibitors, Prem Mohan, et al., pp. 139–150.

*Primary Examiner*—James H. Reamer
*Attorney, Agent, or Firm*—Charlotte L. Barney

[57] ABSTRACT

The oligomers of the present invention are polyesters having a number average molecular weight of <10,000. These oligomers are water-soluble, have a rigid backbone with a predictable anion spacing, and are pharmaceutically-acceptable. The oligomers are useful for the treatment and/or diagnosis of HSV and HCMV.

6 Claims, No Drawings

ANTI-HERPES VIRUS AND CYTOMEGALOVIRUS POLYESTER OLIGOMERS

CROSS REFERENCE TO RELATED APPLICATIONS

The present application is a division of PCT/US91/04804 which was filed on Jul. 8, 1991, designating the United States and which entered the U.S. National phase on Jul. 7, 1993, under 35 U.S.C. 371 and was assigned Ser. No. 07/965,248, and that application is a continuation-in-part of application Ser. No. 07/710,370, filed Jun. 10, 1991, issued Jan. 4, 1994, as U.S. Pat. No. 5,276,182, which is a continuation-in-part of application Ser. No. 7/549,782, filed Jul. 9, 1990, now abandoned; all of which are herein incorporated by reference.

BACKGROUND OF THE INVENTION

This invention relates to the use of certain oligomers in the treatment of diseases caused by Herpes Simplex Virus (HSV) Types 1 and 2 and by Cytomegalovirus.

Research worldwide is currently underway to develop treatments and cures for Herpes Simplex Virus (HSV) Types 1 and 2. Both HSV Types 1 and 2 show a predilection for infection of the ectodermal tissues wherein such infections by the virus cause lesions in the skin, oral cavity, vagina, conjunctiva, and the nervous system. Generally, infection by HSV Type 1 (HSV1) is associated with oral, facial and ocular lesions. Infection by HSV Type 2 (HSV2) generally results in genital and anal lesions. HSV infections left untreated often lead to blindness, neonatal deaths, and encephalitis. HSV Type 2 infections are at an epidemic portion in the US from venereal transmission. Greater than some twenty million persons are presently afflicted with the disease in this country with new cases and recurrences exceeding half a million annually. The annual cost of HSV infections results in a substantial economic loss to diagnose and treat. Epidemiological control of HSV is poor because the majority of the population, up to 90%, has been exposed to the virus.

Man serves as the natural host for HSV Types 1 and 2 infections whereby the virus is transmitted during close personal contact. Initial or primary infections by HSV Types 1 and 2 are contracted through breaks in the mucus membrane. In the healthy carrier the virus can be isolated in the tears, saliva, vaginal and other secretions, even during the absence of overt disease. From the mucus membrane they are able to replicate and spread to the regional lymph nodes. Occasionally these viruses can infect cells of the haemopoietic system and cause viremia.

Part of the difficulty in treating HSV infections results from the ability of these viruses to persist in a latent, or quiescent form. When the primary infection subsides or recedes, the virus generally resides in a latent form in the sensory nerve ganglia which innervate the site of primary infection. In ocular or oral infections with HSV Type 1, the virus generally resides in the trigeminal ganglia. In HSV Type 2 the virus generally resides in the sacral ganglia serving the genitalia and lower abdoman. The determinative period of latency of the HSV virus is unknown, other than this period can be upset by heat, cold, sunlight, hormonal and emotional disturbances, or by immunosuppressive agents, resulting generally in a recurrent infection.

Treatment of HSV infections have largely been ineffective. A number of strategies to stop the virus have been developed. These agents generally inhibit any one of a number of specific viral functions such as (1) adsorption, (2) uncoating, (3) transcription, (4) protein synthesis, (5) nucleic acid replication, (6) maturation, and (7) release.

Most of the antiviral agents thus far used to treat HSV infections have been compounds that interfere with viral DNA. These compounds include Idoxuridine, Cytosine Arabinoside, Adenine Arabinoside, and Trifluorothymidine. Such agents also interfere with similar host functions which results in general problems with cell toxicity and systemic use in humans. Presently, acyclovir is the preferred medication to treat infections with HSV1 and HSV2 due to its potent antiviral effect and negligable toxicity. Poor solubility at high dosage and the emergence of drug-resistant viruses, however, limit the use of this drug.

A number of RNA and DNA containing viruses have envelopes into which virus-coded glycopeptides are incorporated. HSV and cytomegalovirus (CMV) are two such enveloped viruses. Infection of a host cell by enveloped viruses initially relies on the interaction of various receptors on the host cell surface with the envelope glycoproteins of the viral membrane. Subsequently the virus and cell membranes fuse and the virion contents are released into the host cell cytoplasm. The glycoprotein containing envelope of the virus plays an important role in both the initial interaction of the virion and the host cell and in the later fusion of the viral and host cell membranes. The viral envelope seems to be derived from the cellular membrane, but the specificity is due to the viral encoded glycopeptides. Therefore, an inhibitor capable of interfering with the formation of the virus-specific membranes may prevent formation of infectious progeny virus.

SUMMARY OF THE INVENTION

The sulfated oligomers of this invention are represented by any one of the following formulae:

A) a polyurea of the formula:

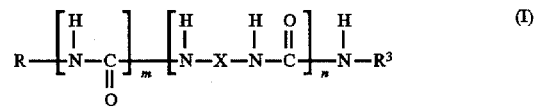

wherein:

R represents a hydrogen atom, a $C_1$–$C_4$ alkyl group, a phenyl group, or a phenyl group substituted with from 1 to 2 $R^1$ moieties and up to 3 substituents independently selected from a chloro or bromo atom or $C_1$–$C_4$ alkyl group;

$R^1$ represents —$SO_3R^2$, —$CO_2R^2$, —$PO_3(R^2)_2$, or —$OPO_3R^2$;

$R^2$ represents represents a hydrogen atom or a pharmaceutically-acceptable cation;

m is an integer 0 or 1, with the proviso that when m is 0, R is a hydrogen atom;

X represents

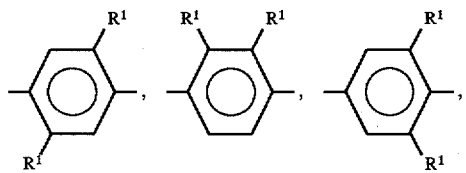

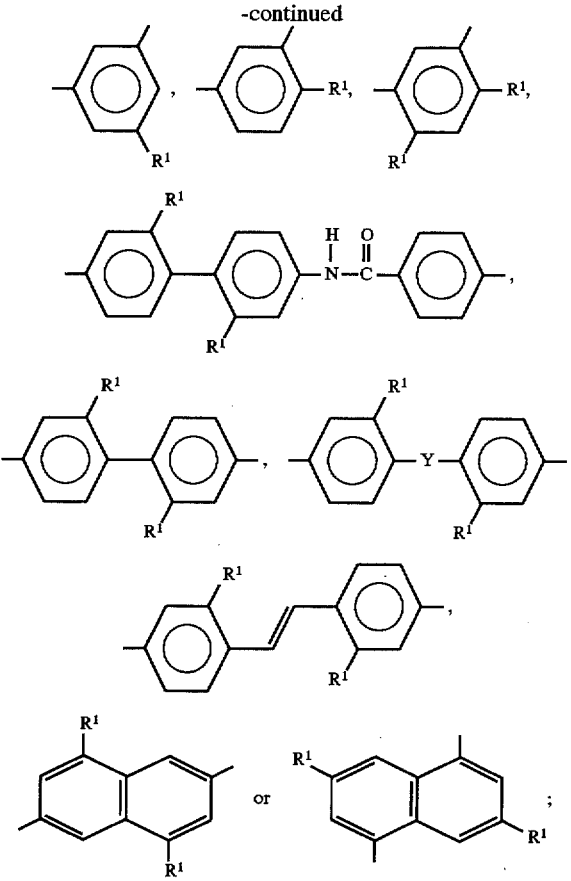

Y represents —CO$_2$—, —C≡C—, —N=N, n is an integer from 3 to 50; and

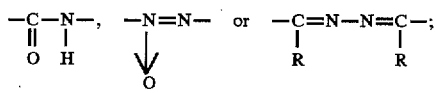

R$^3$ represents —R or —X—NH$_2$, where R and X are defined as before;

B) a polycarbonate of the formula:

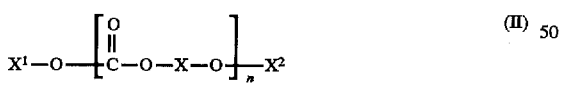

wherein

X and n are defined as in Formula I above;

X$^1$ represents a HO—X— group, where X is defined as for Formula I above, or a C$_1$–C$_4$ alkyl group, a phenyl group, or a phenyl group substituted with from 1 to 2 R$^1$ moieties and up to 3 substituents independently selected from a chloro or bromo atom or C$_1$–C$_4$ alkyl group; and X$^2$ represents a hydrogen atom, or —CO$_2$X$^1$, where X$^1$ is defined as above;

C) a polyester of the formula

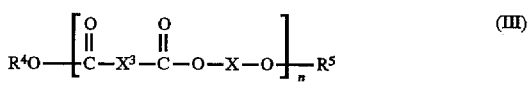

wherein

X and n are defined as in Formula I above;

R$^4$ represents —R$^2$, as defined in Formula I, or —X$^1$, as defined in Formula II above;

R$^5$ represents

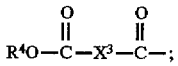

where R$^4$ is defined as in Formula III above, or —R$^2$, where R$^2$ is defined as in Formula I above;

X$^3$ represents

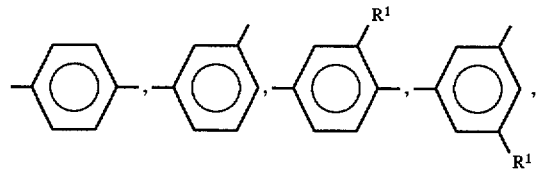

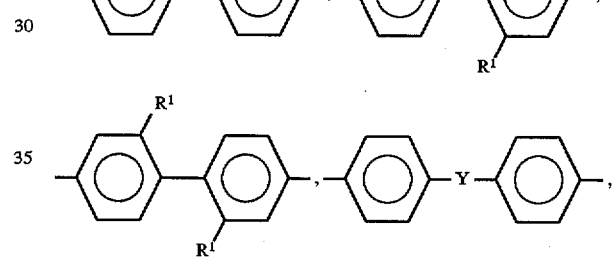

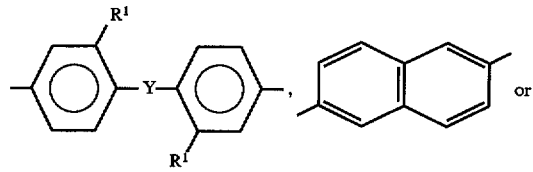

wherein R$^1$ and Y are defined as in Formula I above; or

D) a polyamide of the formula:

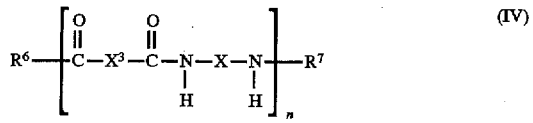

wherein

X and n are defied as in Formula I above;

X$^3$ is defined as in Formula III above;

R$^6$ represents H$_2$N—X—NH—, R$^2$O—, RNH— or R—C(O)—NH—X—NH—, where R, R$^2$ and X are defined as in Formula I;

$R^7$ represents a hydrogen atom,

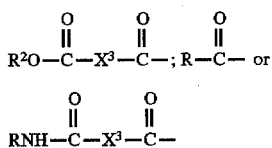

where R and $R^2$ are defined as in Formula I above; and $X^3$ is defined as in Formula III above.

DETAILED DESCRIPTION OF THE INVENTION

The oligomers of the present invention are illustrated by polyureas, polycarbonates, polyesters or polyamides having a number average molecular weight Mn of <10,000 comprising recurring units coupled by carbonyl linking moieties, said oligomer having anionic groups and predominantly linear geometry such that regular spacing between anionic groups exists in an aqueous medium. The oligomers are preferably linear in their backbone and also may be in their salt form. Particularly preferred salts are those that are pharmaceutically acceptable.

The term "pharmaceutically acceptable cation" means a cation acceptable for pharmaceutical use. Those cations that are not substantially toxic at the dosage administered to achieve the desired effect and do not independently possess significant pharmacological activity are included within the term "pharmaceutically acceptable cation". Illustratively, these salts include those of alkali metals, such as sodium and potassium; alkaline earth metals, such as calcium and magnesium; ammonium; light metals of Group IIIA including aluminum; and organic primary, secondary and tertiary amines, such as trialkylamines, including triethylamine, procaine, dibenzylaine, N,N'-dibenzylethylenediamine, dihydroabietylamine, N-($C_1$-$C_4$)alkylpiperidine, and any other suitable amine. Sodium and potassium salts are preferred. The term "pharmaceutically acceptable" means suitable for administration to warm blooded animals, especially human beings, and includes being nontoxic, e.g., suitable for pharmacetucial use and is not poisonous to the warm blooded animal. The pharmaceutically acceptable cations of the oligomers of the present invention are prepared by conventional ion exchange processes or by treating the $R^1$ acid with an appropriate base.

The oligomers of the present invention are low molecular weight, rigid backbone, water soluble polymers. Additionally, the oligomers have ordered anion spacing. By "ordered anion spacing" or "regular spacing between anionic groups" is meant that the anionic groups ($R^1$) are present in the backbone of the polymer at intervals determined by the starting material reagent used and the occurrence of the anionic groups is controlled in a predictable manner. While not wishing to be bound by any theory, the anionic groups of the oligomers are believed to be the portion that binds to the HSV membrane and thereby interrupts the ability of the virus to replicate.

The terms "predominantly linear geometry" in an aqueous medium refers to the solution configuration of the oligomer. A method well known in the art for characterization of the solution configuration of polymer molecules is based on the following formula, referred to as the Mark-Houwink equation ["Introduction to Physical Polymer Science", ed. L. H. Sperling, pub. Joh Wiley & Sons (1985), pp. 81–83], $$[\eta]=KM^\alpha$$

wherein $\eta$ is intrinsic viscosity; M is weight average molecular weight; K is a constant related to chain bond dimension; and $\alpha$ is a constant determined by polymer configuration. The intrinsic viscosity ($\eta$) for a random coil polymer is $0.5<\alpha<0.9$; and for a linear polymer is $0.98<=\alpha<1.8$. This formula relates the solution viscosity "$\eta$" to the molecular weight "M". For this invention linear polymers are defined as having "$\alpha$" values greater than or equal to 0.9. For a rigid rod polymer the theoretical upper limit is 1.8. For a given molecular weight, a higher solution viscosity will be obtained from polymers with a linear configuration relative to those polymers which exist as a random coil. An additional consideration is that the "$\alpha$" value is a function of the solvent used. The "$\alpha$" for a given water soluble polymer may be different at different salt concentrations. For this invention, the salt concentration is set at the levels present in serum (approximately 80 g/L NaCl, 4 g/L KCl).

As used herein, the term "oligomer" encompasses all the possible values for n, e.g., 3 through 50. The oligomers are preferably linear with n equal to an integer from 3 to 50, preferably from 3 to 20, more preferably from 3 to 15. Of course, the n value is directly related to the molecular weight of the resulting oligomer. It is essential that these oligomers are of sufficiently low molecular weight in order to pass through the renal excretory membrane, but able to inhibit the virus. The average molecular weight is governed by the stoichiometry of the reagents. The number average molecular weight (Mn) is <10,000, preferably from about 400 to about 10,000, and most preferably from about 1,000 to about 6,000.

For the purpose of the present invention, the oligomers described herein and physiologically acceptable salts thereof are considered equivalent. Physiologically acceptable salts refer to the salts of those bases which will form a salt with at least one acid group of the $R^1$ group and which will not cause significant adverse physiological effects when administered as described herein. Suitable bases include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary and tertiary amines and the like.

Preferred terms for the previously described Formulae I to IV are as follows:

R and $R^3$ are a 4-methylphenyl group;

m is 1;

n is 3 to 15;

$R^4$ and $R^5$ are hydrogen;

$R^6$ is phenyl;

$R^7$ is benzoyl;

$X^1$ is a 4-methylphenyl group;

$X^2$ is —$CO_2$—(4-methylphenyl) group;

$X^3$ represents

X represents

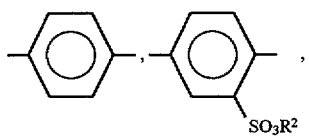

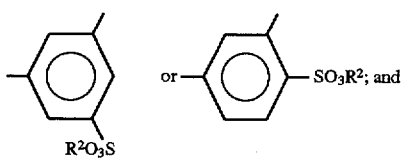

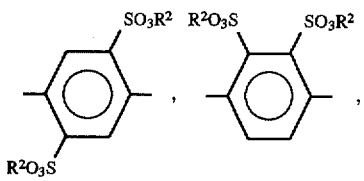

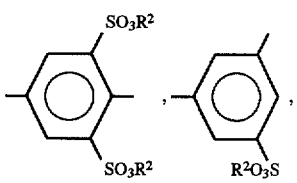

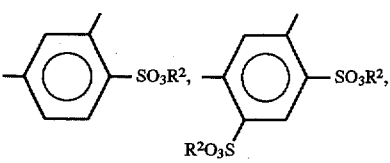

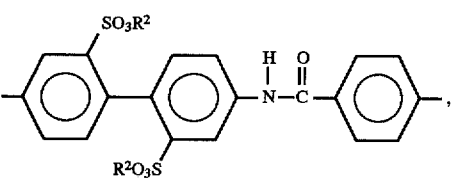

The oligomers were prepared by modifying the procedure of Kershner (U.S. Pat. No. 4,895,660, the disclosure of which is hereby incorporated by reference, and described further below) by replacing a portion of one of the difunctional monomers with a mono-functional end-capping agent and running the reaction in the absence of a surfactant. The number average molecular weight ($M_n$) is governed by the stoichiometry of the reactants.

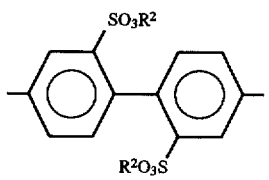

or

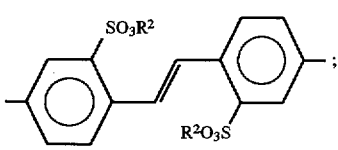

while especially preferred is

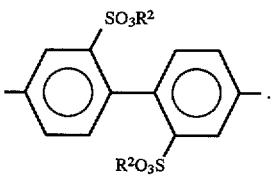

The oligomers of the present invention are prepared by the various reactions described below.

Polyureas and Polyamides (of Formulae I and III above)

The preferred process for the polyureas and polyamides of Formulae I and III above is described in the art (Kershner U.S. Pat. No. 4,824,916) and is further explained as follows. The various reactants and conditions are also described.

Diamines: A wide variety of aliphatic and aromatic diamines are included. The hydrocarbylene diradicals of which the diamines are composed can include methylene, ethylene, butylene, isopropylidene, phenylene, biphenylene, and other diradicals. The range of possible substituents is similarly broad, and includes hydroxyl, alkenyl, lower alkyl moieties, carboxylate, sulfonate, and halogens. The substituents are not necessarily anionic at neutral pH in water.

Difunctional Electrophiles: Phosgene (carbonyl dichloride), carbonyl dibromide, $Cl_3COCOCl$, $Cl_3COCO_2CCl_3$, diacid halides of aliphatic and aromatic dibasic acids such as oxalic, malonic, succinic, glutaric, adipic, sebacic, phthalic, isophthalic, 2,6-naphthalic acids.

Acid Acceptors: Several bases have been employed, such as sodium carbonate, sodium hydroxide, and tributylamine.

Miscellaneous additives: Various surfactants may be added. Suitable surfactants may be non-ionic, such as sorbitan monolaurate, sorbitan monostearate, ethylene glycol distearate, polyethylene oxy/polypropylene oxy polymer. Such surfactants can be difficult to remove from the product, and therefore the use of surfactants is not preferred.

Solvents: Single solvent process employ polar aprotic solvents such as N,N-dimethylacetamide and N,N-dimethylformamide. Also applicable are a combination of water and a second solvent, such as toluene, carbon tetrachloride, benzene, acetone, ethylene dichloride, and the like. Typical ratios of organic to aqueous solvents are about 0.5 to about 2.

In the processes described in the art, the diacid halide is added to a stirred solution or suspension of the other starting materials. In some instances the base is added during the carbonyl dihalide addition. The temperature is maintained between 0° and 50° C., preferably 20° to 30° C. A reactant ratio (molar ratio of diamine to diacid halide) from about 0.9 to 1.2 may be used, with essentially equimolar amounts preferred.

The reaction is stirred at a rate sufficient to achieve mixing of the reactants. The reaction rate is dependent in part on the interfacial area between the phases, and therefore vigorous stirring is preferable. A commercial blender may be employed for this purpose.

The process used to prepared the polyureas of the present invention is a modification of the process described above.

Diamines: The diamines of the present invention are primarily aromatic, with the formulas described in previous sections. Such diamines are substituted with at least one group which is charged at neutral pH, preferable sulfonate. Monovalent aliphatic substituents are allowable. A small set of aliphatic linking groups which tie aromatic radicals together may be used such as trans-substituted ethylene and acetylene. Preferred diamines are those in which the carbon-nitrogen bonds are forced to be parallel, such as PDS, BPDS, StDS, and 2,5-diaminobenzensulfonic acid.

Difunctional electrophiles: For the preparation of polyureas phosgene (carbonyl dichloride) and carbonyl dibromide, and other urea precursors such as carbonyl diimidazole, hexachloroacetone, $Cl_3COCO_2CCl_3$, $CCl_3COCl$, and $Cl_3OCOCl$ may be used. For the preparation of polyamides, aromatic diacids such as isophthalic and terephthalic acid (TPC), 2,6-napthalenedioic acid. These diacids may have neutral or charged substituents, such as monovalent alkyl radical (methyl, ethyl, butyl) and/or charged groups such as sulfonates, phosphates and the like. An example of such a charged difunctional electrophile is sodium 2,5-bis(chlorocarbonyl)benzenesulfonate (TPCS).

Acid Acceptors: A variety of inorganic bases may be used, such as alkali metal or divalent metal hydroxides carbonates, bicarbonates, phosphates. Acid acceptors with buffering capacity are preferred when all of the base is added prior to the addition of the difunctional electrophile. Organic bases such as trialkyl amines may be used, but are not preferred.

Monofunctional end capping agent: A variety of such molecular weight limiting agents may be used. Such agents may be aliphatic or aromatic compounds which react with the diamines or the difunctional electrophiles. Examples of suitable monofunctional agents are amines such as aniline, methylaniline, methylamine, ethylamine, butylamine, diethylamine, ammonia N-methylaniline, phenol and cresol. Examples of monofunctional amine reactive agents are benzoyl chloride, methyl benzoyl chloride, acetyl chloride, and phenyl chloroformate. These end-capping agents may also contain charged substituents, for example potassium 2-sulfophenol or potassium 4-sulfoaniline.

Miscellaneous additives: The addition of surfactants is not necessary or preferred, and can complicate the isolation process.

Solvents: A single solvent, water, is preferred when the difunctional electrophile is a liquid at the reaction temperature. An example of such a difunctional electrophile is phosgene. When solid, water insoluble reactants are used, a small amount of a water immiscible cosolvent is desirable. For example, when terephthaloyl chloride is used a minimum amount of methylene chloride is added to improve the contact between the reactants. Example of such water immiscible cosolvents are chloroform, carbon tetrachloride, toluene, and methylene chloride. Typical ratios of organic to aqueous solvents are 0 to 1, with 0 to 0.1 preferred.

The process is conducted at temperatures which allow the reaction to proceed, typically from about 0° to 100° C. Preferable temperatures are 0° to 25° C. When low boiling starting materials are used, for example phosgene (bp 6° C.), it is advantageous to operate at temperatures at or below the boiling point. The pressure is not important and typically ambient pressure is employed. The pH of the reaction must be carefully maintained for optimum process. At low pH (<6) the reaction is very slow, while at high pH (>10) the difunctional electrophile is unstable to attack by hydroxide or other base. Degradation of the polyurea can also occur at high pH. The pH is preferably maintained between 7 and 9.

When no end capping agent is used, molecular weight control can be achieved by careful adjustment of the stoichiometry of the reactants. Either the diamine or the difunctional electrophile may be used in excess, for example from 1 to 100% molar excess. This stoichiometry must account for any of the difunctional electrophile which is destroyed by hydrolysis prior to reaction with the diamine. For example, when phosgene is used at high pH, a large excess is required to compensate for the fast reaction with hydroxide which destroys it. Because the extent of this side reaction is difficult to control, a monofunctional end capping agent is preferably used to control the molecular weight. Although the techniques mentioned can be used to control the number average molecular weight, the products are mixtures of polymers with several molecular weights characterized by a distribution.

The order of addition of the reactants is not critical. However, the preferred order is to add the difunctional electrophile first. When acid acceptors which are not buffers are used, such as hydroxide, it is most preferable to add a portion at the beginning to achieve the desired pH, and then add the remainder concurrently with the difunctional electrophile.

Finally, it is desirable to conduct these polymerizations at high concentrations. This reduces the amount of solvent which must be removed to isolate the product. Also, in certain cases the product precipitates from the reaction solution near the end of the reaction, and may be isolated by simply decanting the solvent. Most of the inorganic salt which results from reaction of the acid acceptor is removed in this process. The concentration is not critical, and may be from 0.5 to 50 wt %, expressed as weight of diamine to weight of solvent. A preferred range is 5 to 20 wt %.

The product may be isolated by precipitation of the reaction solution into a solvent which is water miscible but is a poor solvent for the product. Examples of such solvents are acetone, methanol, ethanol, isopropanol.

Polycarbonates and Polyesters (of Formulae II and IV above)

The process previously described for the polyureas and polyamides was used, with the following exceptions: Diphenols were used in place of the diamines: Suitable aromatic diphenols containing at least one substituent which is anionic at pH 7. These diphenols have identical structures to those of the diamines except that the amines are replaced with hydroxyl groups. It is possible to pretreat the diols with one or two moles of base to form the mono- or diphenoxides. Some specific examples are dipotassium 4,4'-dihydroxy(1,1'-biphenyl)-2,2'-disulfonate (HBPDS) and dipotassium 2,5-dihydroxy-1,4-benzenedisulfonate (HBDS).

The process conditions are much more critical due to the instability of the products in aqueous solutions. Of particular importance is pH control. At pH levels below 7 the polymerization rate is very slow, while at high pH (>9) the carbonate or ester groups in the polymer undergo hydrolysis. A preferred pH range is 7 to 8, and it is desirable to have an automatic pH controller to maintain it. The useful range of temperatures under which the polymerization can be conducted is more narrow, 0° to 40° C., and preferably from 0° to 25° C.

After addition of the diacid chloride is complete, it is desirable to wait for a time, typically 15 to 120 minutes to insure that the conversion of starting materials is complete. Additional base may be added during this period, but the pH is never allowed to rise above the previously described limits. The product is isolated as a distribution of products as described above.

Herpes Virus Infections

The ability of the sulfated oligomers of this invention to act as anti-viral agents can be demonstrated by their ability to inhibit the growth and replication of HSV virus. Used herein the term "a method of treating a Herpes viral infection" refers a patient who as been in infected with the Herpes virus, either type 1 or type 2, and administering to said patient a virally effective amount of a compound of formulae (I–IV). Futhermore, it is also understood that the term "viral infection" refers to any state or condition characterized by the virus residing in the cells or body of said patient.

Antiviral activity of the compounds of formula (1) can assessed by the plaque-reduction assay as previously described by Tyms et al., J. Antimicrobial Chemotherapy, 8, 65–72 (1981). Briefly, human embryonic fibroblast cells (MRC5) were cultured in 24-well tissue cultrue trays in the presence of Eagles' minimum essential medium (MEM) supplemented with 10% fetal calf serum. When cell monolayers were semi-confluent, they were inoculated with 30–50 plaque-forming units of HSV2 strain HG52 or HSV1 strain 17i (Davison & Wilkie, J. General Virology, 55, 315–331 (1981). At the end of an adsorption period of one hour at room temperature, infected monolayers were overlayed with MEM containing 2% fetal calf serum, 0.5% low-temperature gelling agarose and the antiviral compound at a range of concentrations. After 3 days incubation, cells were fixed in 10% formalin in saline and subsequently stained with 0.3% methylene blue. Dose-response lines were plotted from the mean number of plaques present versus the log of the concentration of the compound. The 50% effective dose (ED50) was computed after linear regression analysis.

Applicants consider the use of the sulfated oligomers of this invention to treat HSV infections in humans to be of most importance. The term "patient" used herein is taken to mean mammals such as primates, including humans, sheep, horses, cattle, pigs, dogs, cats, rats and mice. The applicants refer to the term Herpes viral infection used herein to mean infections caused by either by the Herpes Type I Virus or the Herpes Type 2 Virus.

The amount of the sulfated oligomer of formulae (I–IV) to be administered can vary widely according to the particular dosage unit employed, the period of treatment, the age and sex of the patient treated, the nature and extent of the disorder treated, and the particular sulfated oligomer selected. Moreover the sulfated oligomer can be used in conjunction with other agents known to be useful in the treatment of HSV and CMV infections and agents known to be useful to treat the symptoms of and complications associated with diseases and conditions caused by virus. The anti-Herpes virally and anticytomegalo-virally effective amount of sulfated oligomer of formula 1 to be administered will generally range from about 15 mg/kg to 500 mg/kg. A unit dosage may contain from 25 to 500 mg of sulfated oligomer, and can be taken one or more times per day. The sulfated oligomer can be administered with a pharmaceutical carrier using conventional dosage unit forms either orally, parenterally, or topically.

The preferred route of administration is oral administration. For oral administration the sulfated oligomer can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The sulfated oligomer of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethylene-glycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the sulfated oligomer of formula 1 in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The sulfated oligomer of this invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the sulfated oligomer or it's pharmaceutical salt from about 0.1 to about 10% w/v (weight per unit volume).

Definitions

The terms used in the present application are defined as follows:

n represents the number average repeat length of the distribution through all formulae.

DHPG means Gancicloiur.

pfu means plaque forming units.

MDL 101,028 means poly{imino[2,2'-disulfo(1,1'-biphenyl)-4,4'-diyl]iminocarbonyl}, alpha-{[(4-methylphenyl)amino]-carbonyl}-omega-[(4-methylphenyl) amino]— and is represented by Formula I above when R is 4-methylphenyl, $R^2$ is hydrogen, X is

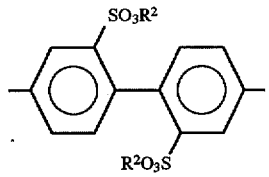

and n is 6.

MDL 101,508 means poly{imino[2,2'-disulfo(1,1'-biphenyl)-4,4'-diyl]iminocarbonyl}, alpha-{[(4-methylphenyl)amino]-carbonyl}-omega-[(4-methylphenyl) amino]— and is represented by Formula I above when R is 4-methylphenyl, $R^2$ is hydrogen, X is

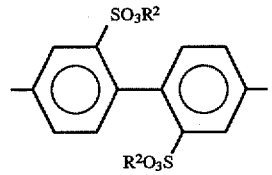

and n is 9.

MDL 29,900 means poly{imino[2,2'-disulfo(1,1'-biphenyl)-4,4'-diyl]iminocarbonyl}, and is represented by Formula I above when m is 0, R is hydrogen, $R^2$ is sodium, X is

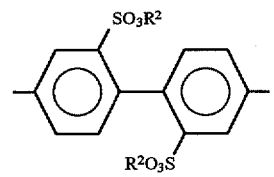

$R^3$ is

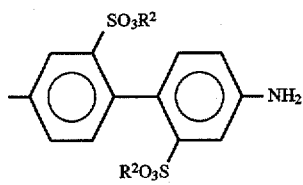

and n is 100.

The following examples illustrate various aspects of the present invention:

EXAMPLE 1

Effect of MDL101028 (U6) on HCMV Replication

Monolayers of MRC5 cells were grown to confluency 24 well tissue culture plates. Virus (AD169/HCMV) was adsorbed in the presence of either test compound or DHPG for 2 hours at room temperature. The inoculum was removed and replaced with an agarose overlay containing the appropriate concentrations of drug. After 10 days incubation at 37° C., cells were fixed in 10% formalin and stained with methylene blue after removal of the agarose. Plaque counts were performed, the percentage inhibition calculated and $ED_{50}$ values computed after linear regression analysis.

| COMPOUND | CONC. | PLAQUE COUNTS | MEAN COUNT | % CONTROL |
|---|---|---|---|---|
| Virus control | — | 212, 204, 182, 199 | 199 | 100% |
| Test Compound µg/ml | 2.4 | 0, 0, 0, 0 | 0 | 0% |
|  | 1.2 | 0, 0, 0, 0 | 0 | 0% |
|  | 0.6 | 1, 0, 1, 0 | 0.5 | 0.25% |
|  | 0.3 | 17, 8, 7, 19 | 12.5 | 6% |
|  | 0.15 | 68, 84, 26, 50 | 57 | 29% |
| DHPG µg/ml | 1.0 | 14, 30 | 22 | 11% |
|  | 0.5 | 41, 41 | 41 | 20% |
|  | 0.25 | 71, 59 | 62 | 31% |
|  | 0.125 | 82, 78 | 80 | 40% |

EXAMPLE 2

Effect of 29,900, 101,028, and 101,508 on the Replication of HSV-2

Vero cells were grown to confluency in 24 well tissue culture plates. The cells were infected with HSV-2 at a multiplicity of infection of 50-pfu/well. The infection was carried out either in the presence or absence of different concentrations of compound. After a 2 hour absorption at room temperature the inoculum was removed and the cells incubated with an agarose overlay containing the appropriate concentration of compound. After 2 days at 37° C. the cells were fixed and stained with methylene blue. The plaques were counted and the percentage inhibition calculated for each concentration of compound. The $ED_{50}$ for each compound was calculated using linear regression analysis.

| HG52 STRAIN HSV-2 | |
|---|---|
| COMPOUND | ED$_{50}$ |
| MDL 29900 (DP) | 0.56 μg/ml |
| MDL 101028 (U6) | 0.29 μg/ml |
| MDL 101508 (U9) | 0.19 μg/ml |

EXAMPLE 3

Tablets are prepared each having the composition:

| MDL 29900 | 250 mg |
|---|---|
| starch | 40 mg |
| talc | 10 mg |
| magnesium stearate | 10 mg |

EXAMPLE 4

Capsules are prepared each having the composition:

| MDL 101028 | 400 mg |
|---|---|
| talc | 40 mg |
| sodium carboxymethylcellulose | 40 mg |
| starch | 120 mg |

EXAMPLE 5

Injectable dosages forms are prepared each having the composition:

| MDL 101508 | 0.500 g |
|---|---|
| polyoxyethylene sorbitan monooleate | 2.000 g |
| sodium chloride | 0.128 g |
| water for injection qs ad | 20.000 ml |

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A method of treating a Herpes viral infection in a patient in need thereof which comprises administering to the patient an anti-Herpes virally effective amount of an oligomer which is a polyester of the formula:

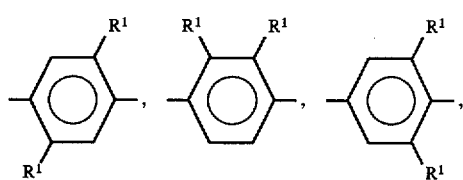

III wherein:

X represents

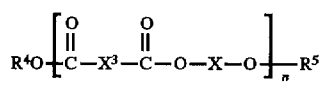

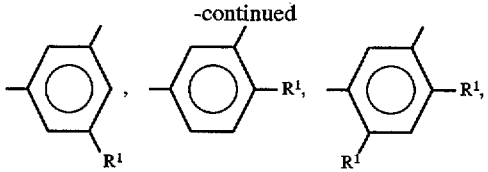

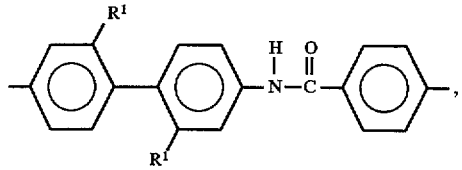

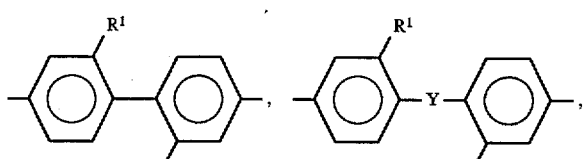

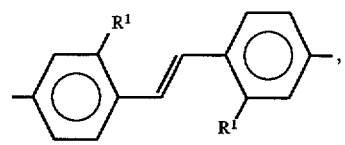

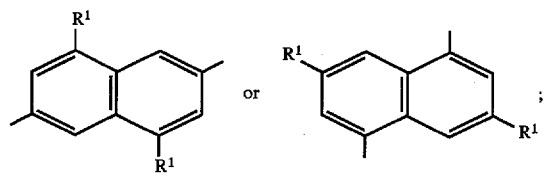

Y represents —CO$_2$—, —C≡C—, —N=N,

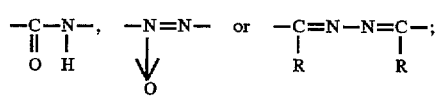

n is 3 to 50;

R$^4$ represents —R$^2$ or X$^1$;

R$^5$ represents

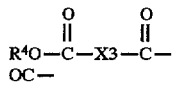

wherein R4 is defined as above

X$^3$ represents

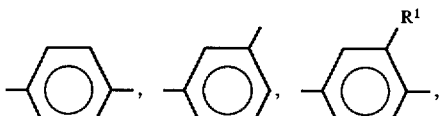

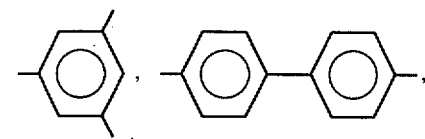

-continued

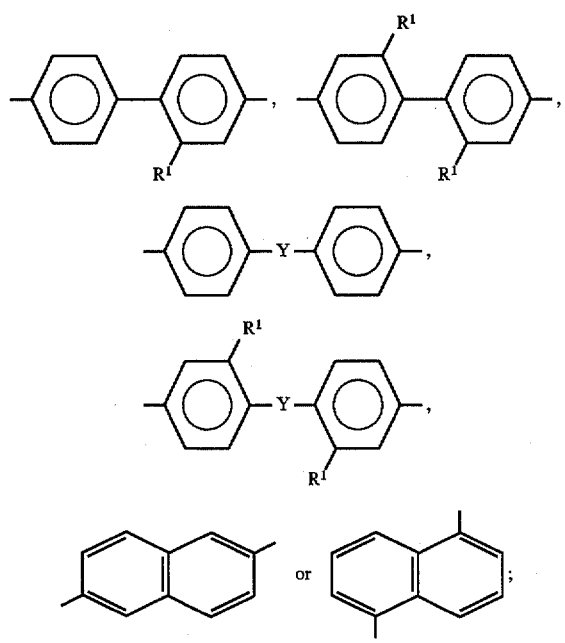

Wherein R' and Y are defined as above $R^1$ represents —$SO_3R^2$, —$CO_2R^2$, —$PO_2(R^2)^2$ or —$OPO_3R^2$;

$R^2$ represents hydrogen or a pharmaceutically-acceptable cation; and $X^1$ represents a HO—X— group, where X is defined as above, or $C_{1-4}$ alkyl, phenyl, or phenyl substituted with from 1 to 2 $R^1$ moieties and up to 3 substituents selected from a group consisting of chloro, bromo, $C_{1-4}$ alkyl.

2. The method of claim 1 wherein $R^4$ and $R^5$ are hydrogen; n is 3 to 15; and $X^3$ represents

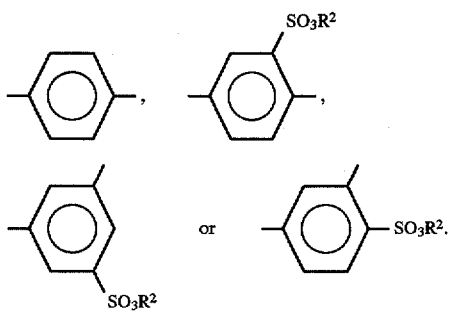

3. The method of claim 1 wherein the oligomer is named as poly{oxy[2,2'-dilsulfo(1,1'biphenyl)-4,4'-diyl]oxycarbonyl-1,4-phenylenecarbonyl}— and is represented by Formula III in claim 1 when $R^4$ and $R^5$ are both hydrogen, $X^3$ is phenylene and X is:

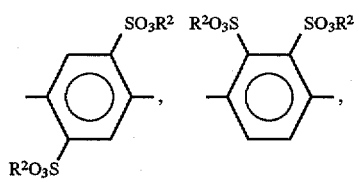

-continued

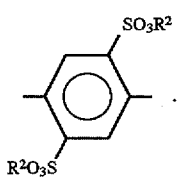

4. The method of claim 2 wherein n is 4.

5. The method of claim 1 wherein the oligomer is named as poly[oxy(2,5-disulfo-1,4-phenylene)-oxycarbonyl- 1,4-phenylenecarbonyl]- and is represented by Formula III in claim 30 when $R^4$ and $R^5$ are both hydrogen, $X^3$ is p-phenylene and X is 6. The method of claim 3 wherein n is 3.

* * * * *

UNITED STATES PATENT AND TRADEMARK OFFICE
CERTIFICATE OF CORRECTION

PATENT NO. : 5,670,144

DATED : September 23, 1997

INVENTOR(s) : Alan D. Cardin, Richard L. Jackson, Michael J. Mullins

It is certified that error appears in the above-identified patent and that said Letters Patent is hereby corrected as shown below:

At column 11, line 3, the patent reads "in infected" and should read --infected--.
At column 11, lines 9 -10, the patent reads "can assessed" and should read --can be assessed--.
At column 11, line 13, the patent reads "cultrue" and should read --culture--.
At column 12, line 30, the patent reads "pharmaceutically adjuvants" and should read --pharmaceutical adjuvants--.
At column 17, line 54, after the structure, the patent should read:

"X represents

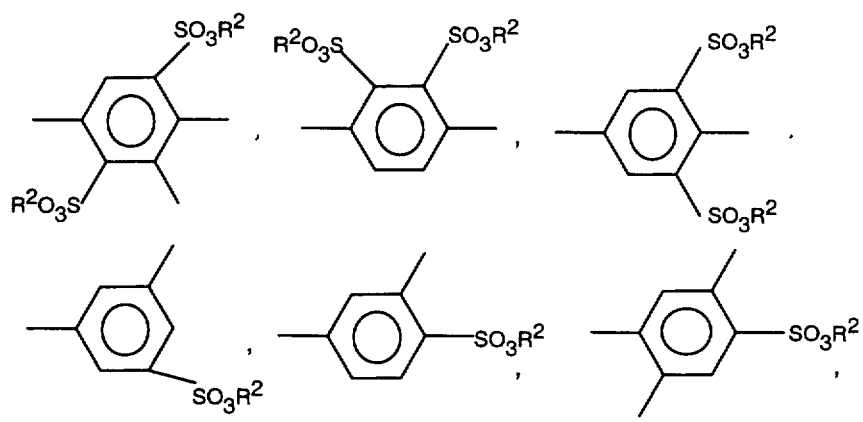

UNITED STATES PATENT AND TRADEMARK OFFICE
CERTIFICATE OF CORRECTION

PATENT NO. : 5,670,144

DATED : September 23, 1997

INVENTOR(s) : Alan D. Cardin, Richard L. Jackson, Michael J. Mullins

It is certified that error appears in the above-identified patent and that said Letters Patent is hereby corrected as shown below:

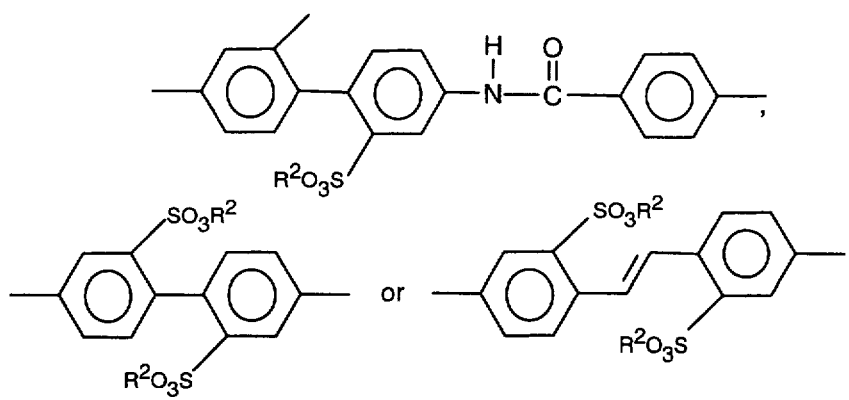

At column 18, line 51, cancel Claim 5.

UNITED STATES PATENT AND TRADEMARK OFFICE
CERTIFICATE OF CORRECTION

PATENT NO. : 5,670,144

DATED : September 223, 1997

INVENTOR(s) : Alan D. Cardin, Richard L. Jackson, Michael J. Mullins

It is certified that error appears in the above-identified patent and that said Letters Patent is hereby corrected as shown below:

Col. 18, delete claim 5 add the following new claim:

-- 5. The method of claim 1 wherein the oligomer is named as poly[oxy(2,5-disulfo-1,4-phenylene)oxycarbonyl-1,4-phenylenecarbonyl)] and is represented by Formula III in Claim 1 when $R^4$ and $R^5$ are hydrogen, $X^3$ is p-phenylene and X is

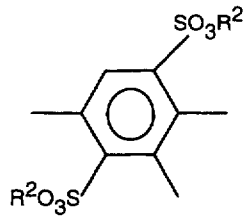

Signed and Sealed this

Fourteenth Day of July, 1998

Attest:

BRUCE LEHMAN

Attesting Officer

Commissioner of Patents and Trademarks